United States Patent [19]

Mattson

[11] Patent Number: 5,493,599
[45] Date of Patent: Feb. 20, 1996

[54] OFF-FOCAL RADIATION LIMITING PRECOLLIMATOR AND ADJUSTABLE RING COLLIMATOR FOR X-RAY CT SCANNERS

[75] Inventor: Rodney A. Mattson, Mentor, Ohio

[73] Assignee: Picker International, Inc., Highland Hts., Ohio

[21] Appl. No.: 300,974

[22] Filed: Sep. 6, 1994

Related U.S. Application Data

[63] Continuation-in-part of Ser. No. 224,958, Apr. 8, 1994, which is a continuation-in-part of Ser. No. 863,182, Apr. 3, 1992, Pat. No. 5,305,363.

[51] Int. Cl.⁶ ........................................ G21K 1/02
[52] U.S. Cl. ....................... 378/147; 378/4; 378/148; 378/150
[58] Field of Search ................... 378/147, 151, 378/160, 121, 134, 148, 9, 14, 15, 16, 4, 150

[56] References Cited

U.S. PATENT DOCUMENTS

| | | | |
|---|---|---|---|
| 4,122,346 | 10/1978 | Enge | 250/398 |
| 4,135,095 | 1/1979 | Watanabe | 250/445 T |
| 4,227,088 | 10/1980 | Maydan et al. | 250/445 T |
| 4,300,051 | 11/1981 | Little | 250/445 T |
| 4,368,535 | 1/1983 | Baumann | 378/15 |
| 4,521,900 | 6/1985 | Rand | 378/137 |
| 5,125,012 | 6/1992 | Schittenhelm | 378/10 |
| 5,179,583 | 1/1993 | Oikawa | 378/135 |
| 5,191,600 | 3/1993 | Vincent et al. | 378/10 |
| 5,200,985 | 4/1993 | Miller | 378/135 |
| 5,241,577 | 8/1993 | Burke et al. | 378/135 |
| 5,305,363 | 4/1994 | Burke et al. | 378/4 |

FOREIGN PATENT DOCUMENTS

| | | | |
|---|---|---|---|
| 377534A1 | 11/1990 | European Pat. Off. | |
| 2244899 | 11/1991 | United Kingdom | 378/4 |

*Primary Examiner*—Constantine Hannaher
*Assistant Examiner*—Don Wong
*Attorney, Agent, or Firm*—Fay, Sharpe, Beall, Fagan, Minnich & McKee

[57] ABSTRACT

A toroidal x-ray tube (I) is supported and selectively positioned by a gantry (II). The x-ray tube includes a toroidal housing (A) in which a rotor (20) is rotatably mounted. One or more cathodes (C) are mounted on the rotor for generating an electron beam which strikes an anode (B) to generate a beam of x-rays which pass through a patient aperture (62) to strike a detector (60). The x-ray tube includes pre-collimators (70, 74) having slots (72, 76) for passage of the x-ray subsequent to generation thereof and prior to being collimated by the collimator (90). A ring collimator (90) collimates an x-rays formed into a fan shaped beam. The collimator (90) includes a first ring (92) and a second ring (94) which are concentric. The distance between the first and second rings (92, 94) is adjustable to adjust the slice thickness of the final image. The x-ray tube provides improved final images in that reduction of off-focal radiation occurs due to the utilization of pre-collimators and the collimation of x-rays is flexible due to adjustability of slice thickness.

21 Claims, 6 Drawing Sheets

OFF-FOCAL RADIATION LIMITING PRECOLLIMATOR AND ADJUSTABLE RING COLLIMATOR FOR X-RAY CT SCANNERS

This application is a continuation-in-part of U.S. application Ser. No. 08/224,958 filed Apr. 8, 1994, pending which is a continuation-in-part of U.S. application Ser. No. 07/863,182 filed Apr. 3, 1992, now U.S. Pat. No. 5,305,363.

BACKGROUND OF THE INVENTION

The present invention pertains to the art of reducing off-focal radiation and collimating in connection with x-ray generation. It finds particular application in conjunction with annular x-ray tubes for CT scanners and will be described with particular reference thereto. However, it is to be appreciated that the present invention will also find application in conjunction with the generation of radiation for other applications.

Typically, a patient is positioned in a supine position on a horizontal couch through a central bore of a CT scanner. An x-ray tube is mounted on a rotatable gantry portion and rotated around the patient at a high rate of speed. For faster scans, the x-ray tube is rotated more rapidly. However, rotating the x-ray more rapidly decreases the net radiation per image. As CT scanners have become faster, larger x-ray tubes have been developed which generate more radiation per unit time to maintain the desired radiation dose at higher speeds. Larger tubes, of course, cause high inertial forces.

High performance x-ray tubes for CT scanners and the like commonly include a stationary cathode and a rotating anode disk, both enclosed within an evacuated housing. As more intense x-ray beams are generated, there is more heating of the anode disk. In order to provide sufficient time for the anode disk to cool by radiating heat through the vacuum to surrounding fluids, x-ray tubes with progressively larger anode disks have been built.

The larger anode disk requires a larger x-ray tube which does not readily fit in the small confined space of an existing CT scanner gantry. Particularly in a fourth generation scanner, incorporating a larger x-ray tube and heavier duty support structure requires moving the radiation detectors to a larger diameter. A longer radiation path between the x-ray tube and the detectors would require that the detectors be physically larger to subtend the required solid angle. Larger detectors would be more expensive. Not only is a larger x-ray tube required, larger heat exchange structures are required to remove the larger amount of heat which is generated.

Rather than rotating a single x-ray tube around the subject, others have proposed using a switchable array of x-ray tubes, e.g. five or six x-ray tubes in a ring around the subject. See, for example, U.S. Pat. No. 4,274,005 to Yamamura. However, unless the tubes rotate, only limited data is generated and only limited image resolution is achieved. If multiple x-ray tubes are rotated, similar mechanical problems are encountered trying to move all the tubes quickly and remove all of the heat.

Still others have proposed constructing an essentially bell-shaped, evacuated x-ray tube envelope with a mouth that is sufficiently large that the patient can be received a limited distance in the well of the tube. See, for example, U.S. Pat. No. 4,122,346 issued Oct. 24, 1978 to Enge or U.S. Pat. No. 4,135,095 issued Jan. 16, 1979 to Watanabe. An x-ray beam source is disposed at the apex of the bell to generate an electron beam which impinges on an anode ring at the mouth to the bell. Electronics are provided for scanning the x-ray beam around the evacuated bell-shaped envelope. One problem with this design is that it is only capable of scanning about 270°.

Still others have proposed open bore x-ray tubes. See, for example, U.S. Pat. No. 5,125,012 issued Jun. 23, 1992 to Schittenhelm and U.S. Pat. No. 5,179,583 issued Jan. 12, 1993 to Oikawa. These large diameter tubes are constructed analogous to conventional x-ray tubes with a glass housing and a sealed vacuum chamber. Such tubes are expensive to fabricate and are expensive to repair or rebuild in case of tube failure.

Copending U.S. application Ser. No. 08/224,958 discloses a ring anode disposed in the housing. An annular rotor is rotatably received in the toroidal housing. At least one cathode is mounted on the rotor for generating an electron beam which strikes the anode target. The rotor and the cathode are rotated such that the electron beam is rotated around the ring anode. X-rays are emitted from a ring anode that is struck by energetic electrons from one of selected cathodes on the rotor. The more precisely the x-rays are collimated into a fan or other preselected shaped beam, the sharper and more artifact free the resultant CT images are.

One consideration is the amount of off-focal radiation produced during generation of the x-ray beam. Off-focal radiation is produced primarily due to energetic backscattered electrons whose energy is comparable to x-rays in locations off of the focal spot. The backscattered electrons tend to cause x-rays to be generated from broad areas of the x-ray anode and any surrounding material that may be at a positive potential relative to the cathode. Off-focal radiation has a negative effect on the image quality of x-ray images, particularly the reconstructed CT images. The off-focal radiation is a broad source of radiation that tends to blur in CT images and to cause more pronounced artifacts in the region of the interface of high and low contrast objects.

Moreover, a fixed collimator attached to the rotating frame within the vacuum enclosure is one method that can create the required fan beam of x-rays. This approach is most effective for fixed single or multiple slice applications in which each cathode assembly has an individual collimator. It is difficult and inconvenient to adjust collimators within a high vacuum. Mechanical adjustment mechanisms increase a risk of vacuum contamination.

The present invention contemplates a new and improved toroidal x-ray tube and CT scanner which resolves the above referenced difficulties and others.

SUMMARY OF THE INVENTION

A large diameter toroidal housing is provided. An annular anode is mounted in the evacuated annular interior of the housing along with a rotating frame assembly. At least one cathode assembly is mounted to the rotating frame for rotation therewith.

In accordance with another aspect of the present invention, a pre-collimator is supported in the interior of the housing. The pre-collimator has a slot for passage of the x-ray beam subsequent to generation thereof.

In accordance with a more limited aspect of the present invention, the pre-collimator is mounted on the rotating frame in alignment with at least one cathode assembly.

In accordance with a more limited aspect of the present invention, a second pre-collimator is supported by the anode. The second pre-collimator includes a second slot for passage of the x-ray beam.

In accordance with another aspect of the present invention, a ring collimator is supported on the exterior of the housing inside the patient aperture for collimating the beam into a fan-shaped beam. The collimator comprises a first ring and a second ring.

In accordance with a more limited aspect of the present invention, the x-ray tube is further provided with an arrangement for adjusting the distance between the first and second rings.

In accordance with another aspect of the present invention, the toroidal x-ray tube is incorporated into a CT scanner.

One advantage of the present invention is that it reduces off-focal radiation.

Another advantage of the present invention is that it produces improved CT images with minimal blurring and artifacts particularly in the region of the interface of high and low contrast objects.

Another advantage of the present invention is that it reduces x-ray bremsstrahlung, undesired deflected electrons, produced if backscattered electrons strike material in the solid angle viewed by the x-ray detection system.

Yet another advantage of the present invention resides in improved collimation.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF THE PREFERRED EMBODIMENTS

Figure 1:
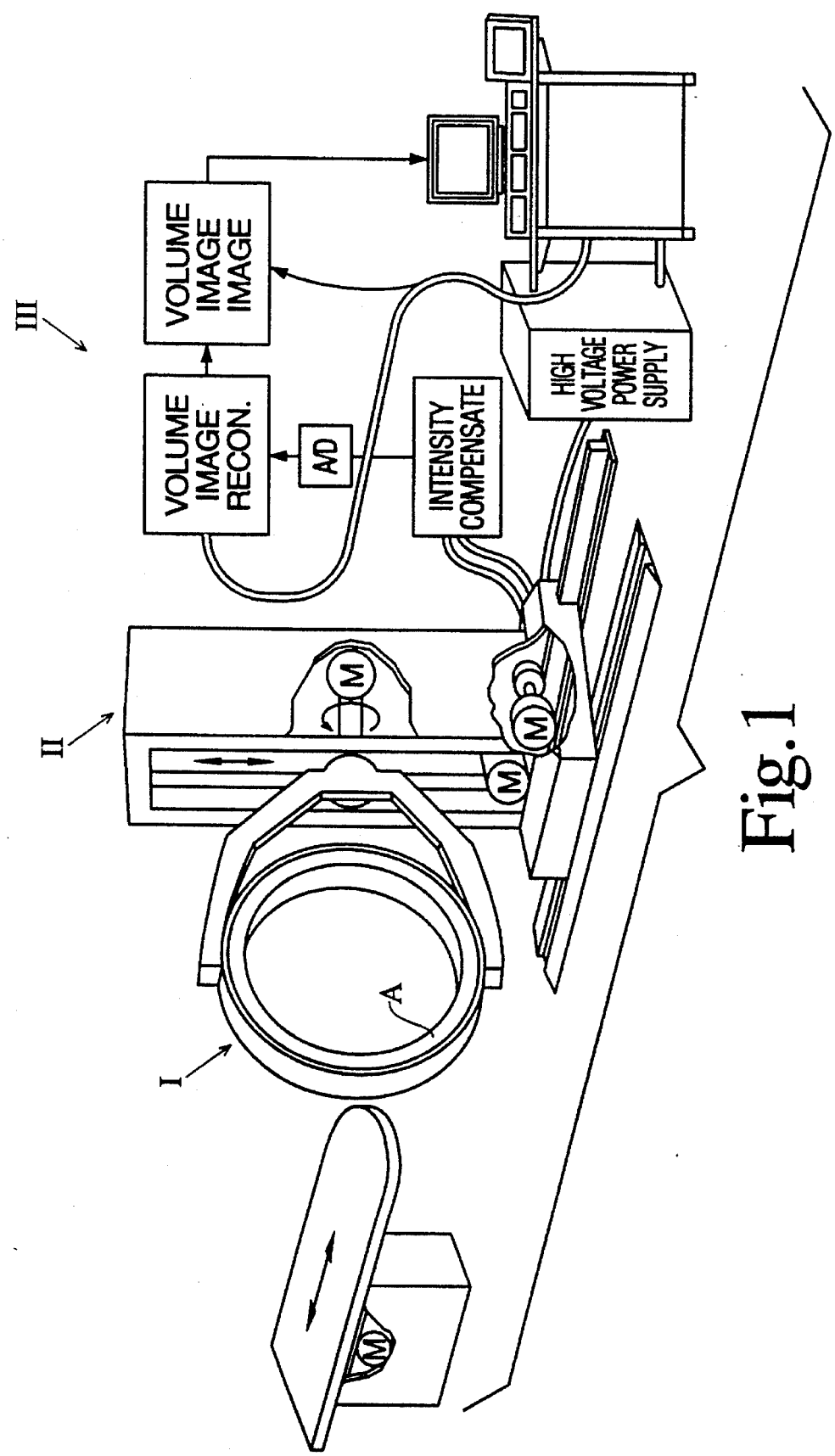
FIG. 1 is a perspective view of a CT scanner system in accordance with the present invention.

With reference to FIG. 1, a CT scanner includes a toroidal ring x-ray tube I which is mounted to a gantry or mechanical mounting assembly II, and an electronics section III. The electronic section provides operating power and control signals to the gantry, receives data from the gantry, reconstructs the received data into an electronic image representation, and converts the electronic representation to human readable form.

Figure 2:
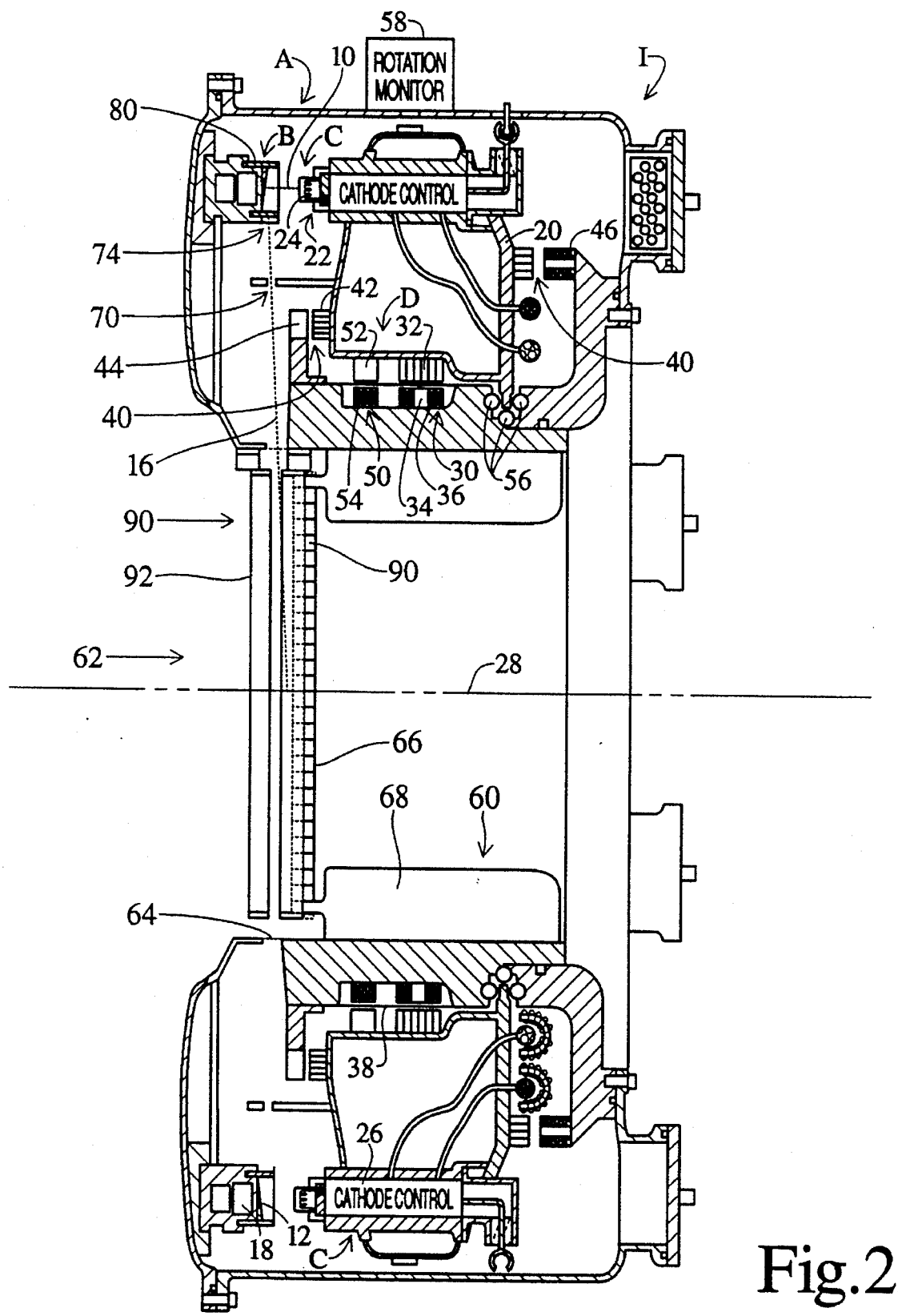
FIG. 2 is a cross-sectional view of the toroidal rotating cathode x-ray tube of FIG. 1.

With reference to FIG. 2, the ring tube I includes a toroidal housing A which defines a large, generally donut-shaped interior volume. A ring anode B is mounted within the toroidal housing interior volume and extends circumferentially therearound. A cathode assembly C is disposed within the toroidal housing interior space for generating at least one beam 10 of electrons. A motor D selectively rotates the cathode or otherwise rotates the electron beam around the anode B.

More specifically, the anode B is a tungsten ring having a tungsten face 12 upon which the electron beam 10 impinges. The interaction of the electron beam 10 and the anode face 12 generates a hemisphere x-ray flux 14 (FIG. 3) for collimation into a usable x-ray beam 16, as described below. The anode assembly defines an annular anode adjacent cooling fluid path or channel 18 in intimate thermal communication with the anode face, specifically along an opposite surface of the anode. Optionally, the anode can have internal passages, fins, and the like to promote thermal communication with the cooling fluid.

A rotor, or rotating frame, 20, such as a rotating annular ring or frame is mounted for rotation around an interior of the toroidal housing A. The rotating frame 20 supports a corresponding plurality of cathode assemblies C. Each of the cathode assemblies includes a cathode cup 22 which contains a filament 24 or other electron source and a cathode control circuit 26. The filament 24 and the anode face 12 are maintained at a high relative voltage relative to each other, e.g. 150 kV. The housing A and the rotating frame 20 are maintained at a common potential, preferably ground potential. In the preferred embodiment, the anode is also maintained at ground potential and the cathode cup is insulated from the rotor 20 and maintained at about −150 kV. Alternately, the anode may be maintained at approximately +75 kV and the cathode at about −75 kV relative to ground.

The rotating frame 20 is rotatably supported within the housing A for rotation about a central axis 28 on a bearing 30, a magnetic levitation bearing in the preferred embodiment. The magnetic levitation bearing 30 includes rings of silicon steel 32, which are stable within the vacuum, mounted along an inner radius of the rotating frame 20. Passive and active elements including permanent magnets 34 and electromagnets 36 are disposed closely adjacent the rings 32 of silicon steel. The housing A includes a magnetic window 38 which separates the vacuum region from the electromagnets 36. The magnetic window, such as an aluminum film, permits magnetic flux to pass but prevents epoxy or other polymers commonly used in coils from outgassing into the vacuum region.

To maintain the alignment of the rotating frame 20, a pair of oppositely disposed magnetic levitation bearings 40 are mounted on opposite sides of the rotor. Each has rings of silicon steel 42 and permanent magnets 44 to provide opposing forces on the rotor. The magnetic levitation bearing on one side also has electromagnetic coils 46 to adjust the relative opposing forces. The electromagnet is again shielded from contaminating the vacuum by an aluminum film or other magnetic window. Position sensors, not shown but conventional in the art, are provided for controlling the electromagnetic coils to maintain the position of the rotor 20 precisely during rotation.

The motor D is preferably a large diameter brushless ring motor 50. The motor includes rotor 52, preferably of permanent magnets, mounted to the rotating frame 20 within the vacuum region. A stator 54, including electromagnetic windings, is positioned directly opposite the rotor 52 but across the magnetic window 38 outside of the vacuum region. Mechanical roller bearings 56, normally out of contact with the rotor, are provided to support the rotor 20 in the event the magnetic levitation system should fail. The mechanical roller bearings prevent the rotor 20 from interacting directly with the stationary housing A and other associated structures. An angular position monitor 58 monitors the angular position of the rotation of the rotating frame 20, hence the angular position of the cathode assemblies and the apices of the x-ray beams precisely.

A detector ring 60 is disposed around a patient aperture 62 that is surrounded by the housing A to detect x-rays that have exited the housing through an x-ray transmissive window 64. The detector ring 60 includes a ring of x-ray detectors 66, such as optically coupled scintillation crystals and photodiodes. A detector electronics section 68 includes preamplifiers, filters, analog-to-digital converters, and the like.

Figure 3:
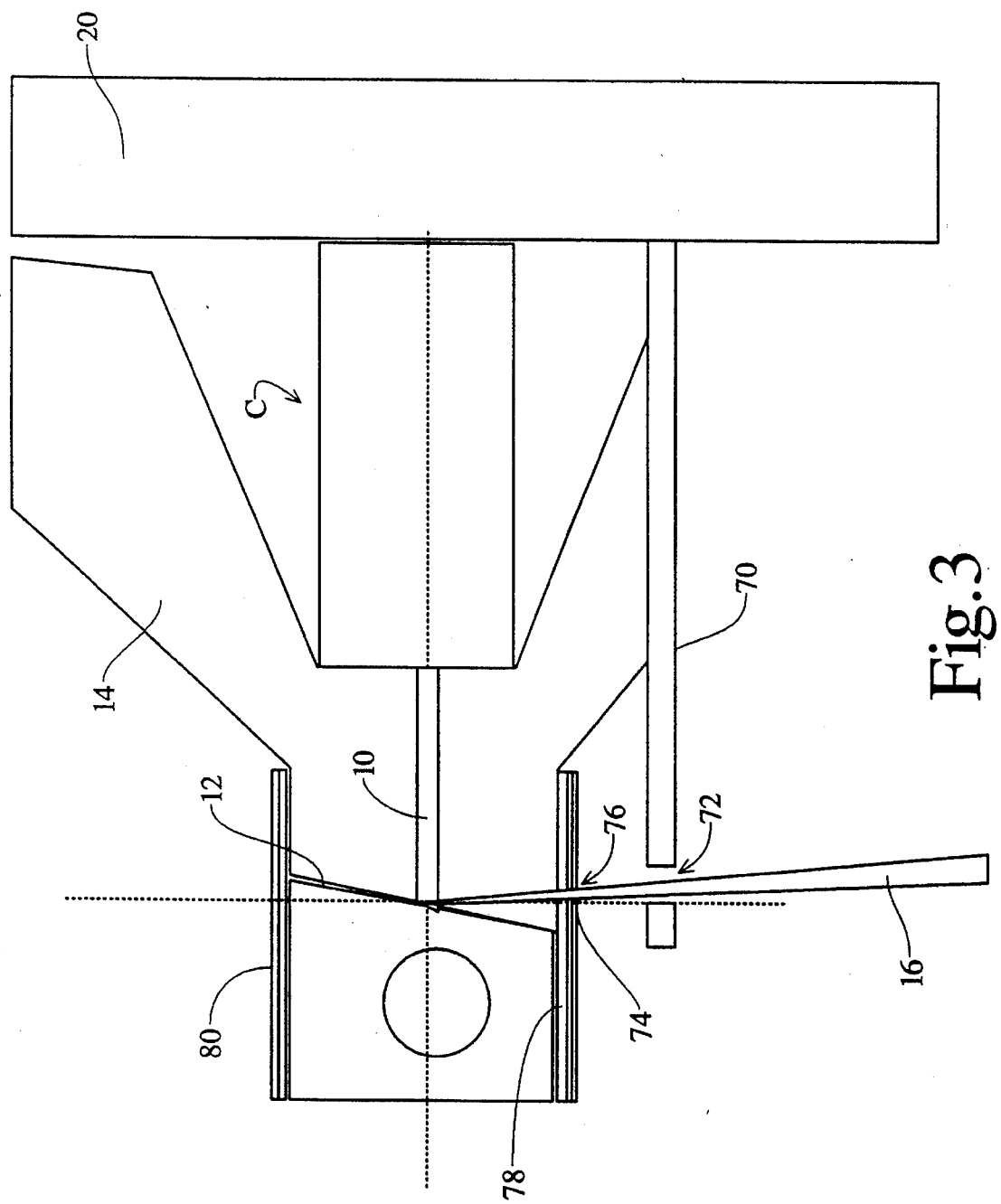
FIG. 3 is an enlarged diagrammatic view of the anode assembly of FIG. 2 illustrating one embodiment of the precollimator.

Referring now more particularly to FIG. 3, along with FIG. 2, an off-focal radiation shield, or pre-collimator, 70 is mounted to the rotating frame 20 in alignment with each cathode C disposed thereon. In the preferred embodiment, eight cathodes and off-focal radiation, or pre-collimator, shields, or pre-collimators, 70 are used.

In the pre-collimator shield 70, an aperture or slot 72 is cut slightly wider than the maximum selectable thickness of the x-ray beam 16. The length of the slot defines the width or arc of the x-ray beam 16. The pre-collimator shield 70 is preferably made of a high z material, such as tantalum or tungsten, and is placed as near to the focal spot as possible to shield the environment from x-rays.

Preferably, the pre-collimator shield 70 is held at a negative potential such that it repells backscattered electrons. This prevents back scattered electrons from interacting with the pre-collimator 70 to produce x-rays. Further, however, it is recognized that the proximity of the pre-collimator 70 to the anode is limited due to their potential difference.

A pre-collimator 74 which is constructed of a high z radiation blocking material is directly mounted to the anode B. The pre-collimator (74) has a window, such as an annular slot 76 that sets a maximum limit on the thickness of the x-ray beam 16. A support structure 78 such as a ring of low z material, supports the portion of the pre-collimator 74 extending beyond the slot 76.

The pre-collimator 74, which is at ground potential and bonded to the anode, limits out-of-plane off-focal radiation seen by the x-ray detection system 60.

In the preferred embodiment, the annular sections that define the slot 76 are bonded with a beryllium sheet 78. The gradient of the electric field generated near the anode focal track allows backscattered electrons to be attracted to the stationary pre-collimator 74. The backscattered electrons that return to the anode B is accordingly reduced. The number of backscattered electrons that strike the beryllium surface produce only 5.5% of bremsstrahlung x-rays usually produced by a tungsten surface.

Beryllium of the thickness required is highly transmissive to x-rays of diagnostic energies and does not adversely affect the x-ray spectrum. The heat produced from the bombardment of backscattered electrons is conducted directly to the anode and is removed from the x-ray tube by the anode cooling water.

A rear or outer peripheral anode shield 80 blocks portions of the x-ray flux 14 from escaping radially outward. Rear anode shield 80 is preferably formed of a high z material, i.e., a high atomic number material, and is disposed on an opposite side of the anode B relative to the pre-collimator 70. The rear anode shield 80 is directly mounted on the anode B in a known manner.

The high z material used in the pre-collimator 74 and shield 80 near the annular anode B is an effective x-ray shield. This strategically located x-ray shield reduces the amount of shielding material needed at more distant locations. The overall weight of the x-ray tube is thus reduced.

In alternative embodiments, different combinations of the pre-collimators 70 and 74 and rear anode shield 80 are used. For example, in one embodiment, only the pre-collimator 70 is provided. In another embodiment, only pre-collimator 74 is utilized. In still yet other embodiments, the rear anode shield is selectively used with the aforenoted, and other, configurations of the pre-collimators.

Figure 4:
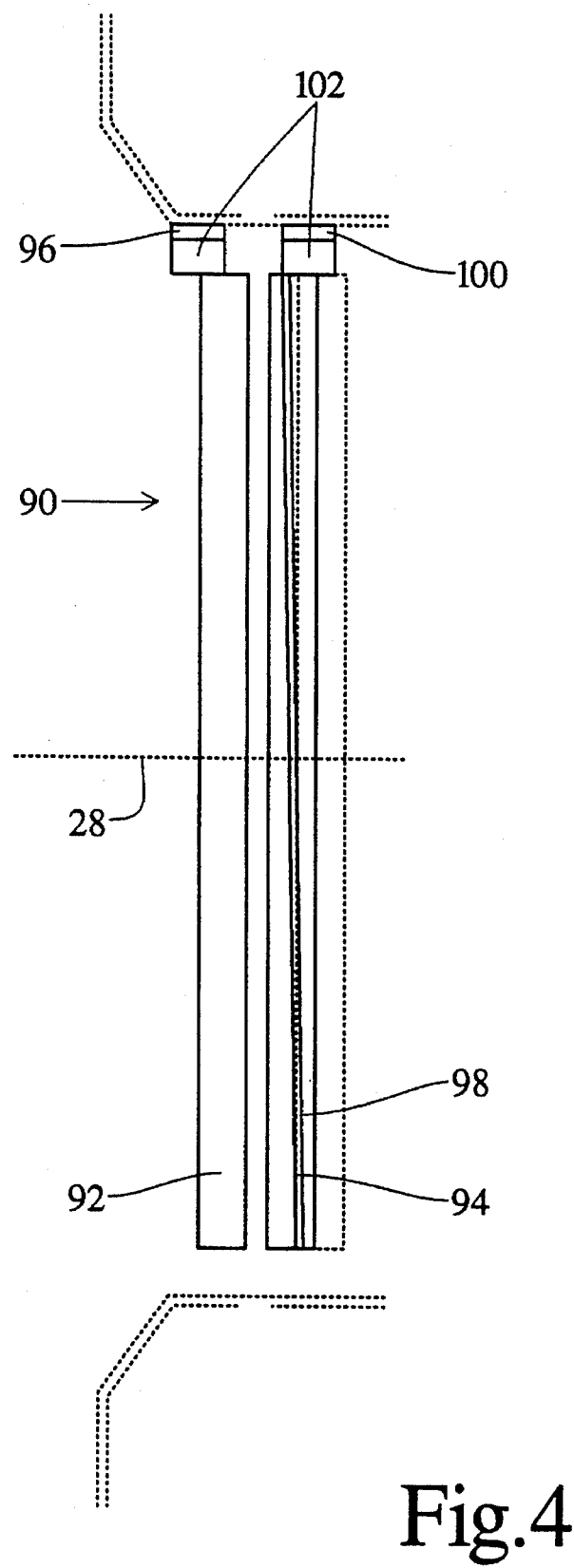
FIG. 4 is an enlarged side view of the ring tube collimator of FIG. 2 incorporating a rotary motion drive mechanism.

Referring now to FIG. 4, a ring collimator 90 includes a fixed ring 92 and a movable ring 94. The movable ring 94 moves toward and away from the fixed ring 92 to adjust a distance therebetween. The distance between the fixed ring 92 and the movable ring 94 determines the x-ray beam thickness hence the slice thickness. The slice thickness is adjusted by translating the movable ring 94 toward the fixed ring 92 for thinner slices and by translating the movable ring 94 away from the fixed ring 92 for thicker slices.

Advantageously, the central position of the x-ray beam is changed one-half the distance of the total adjustment of the movable ring 94. Such repositioning is accomplished using mechanical, electrostatic, and/or electromagnetic adjustment mechanisms and structures.

The fixed ring 92 is positioned on mounting pads 96 with its center coincident with the central axis 28. The geometric plane of the fixed ring is adjusted to be parallel with the geometric plane of tungsten ring anode surface 12, both of which are perpendicular to the central axis. A plane alignment for any one of the cathodes C is typically satisfactory for all the cathodes. Variations in the alignment of the cathodes C on the rotating frame 20 will affect the beam landing track on the ring anode B. The x-ray plane and the fixed ring plane of fixed ring 92 has a constant spacing to preserve the angle of incidence of x-rays with the fixed ring 92. The angle is preferably constant for any cathode C that is selected.

One preferred manner of suitably adjusting the movable ring 94 is to utilize a fine pitch screw thread drive. As shown in FIG. 4, a fine pitch screw thread 98 is machined in the outer periphery of the movable ring 94. A fine pitched screw thread, not shown, is also machined on a mating assembly on a mounting pad 100 attached to the scanner. The linear motion for slice thickness selection is preferably accomplished by rotating the movable ring 94 relative to the mounting pad 100 with a rotary motor drive mechanism 102. Conventional worm or helical gear configurations are preferred for this operation. Alternatively, an annular ring constructed of low density and low atomic materials can be used to join the threaded fixed ring 92 and movable ring 94. It is recognized that thread configurations on the fixed ring 92 and movable ring 94 can be reversed such that the forward ring is movable and the rearward ring is not movable. As yet another option, both rings can move in coordination with each other.

In a further alternative, outer screw threads can be machined directly into the ring tube housing.

In an alternative embodiment, the adjustment means is a linear motion drive mechanism. The linear motion drive mechanism adjusts the gap between the two rings by controlling one or more identical mechanisms that translate the movable ring to suitable positions without the use of threads or the rings. Generally, three or more linear drive mechanisms effectively drive the adjustable ring 94. It is preferred that the linear drive mechanism be capable of positioning the ring to 0.0005 of an inch accuracy.

Figure 6:
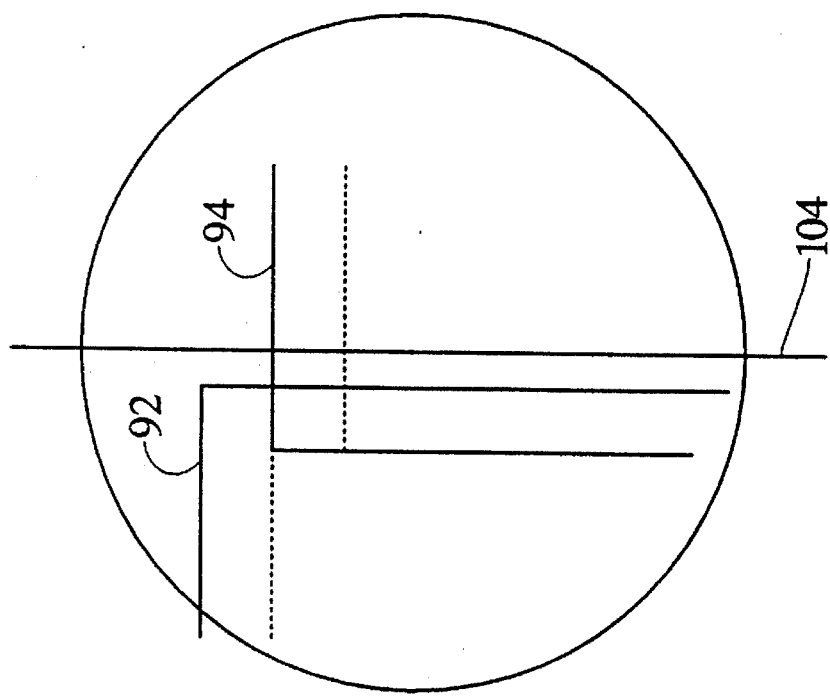
FIG. 6 is a partial cross sectional view of the collimator of FIG. 5 in a closed state; and, FIG. 7 is an enlarged diagrammatic view of an alternative embodiment of an x-ray tube assembly in accordance with the present invention.
Figure 5:
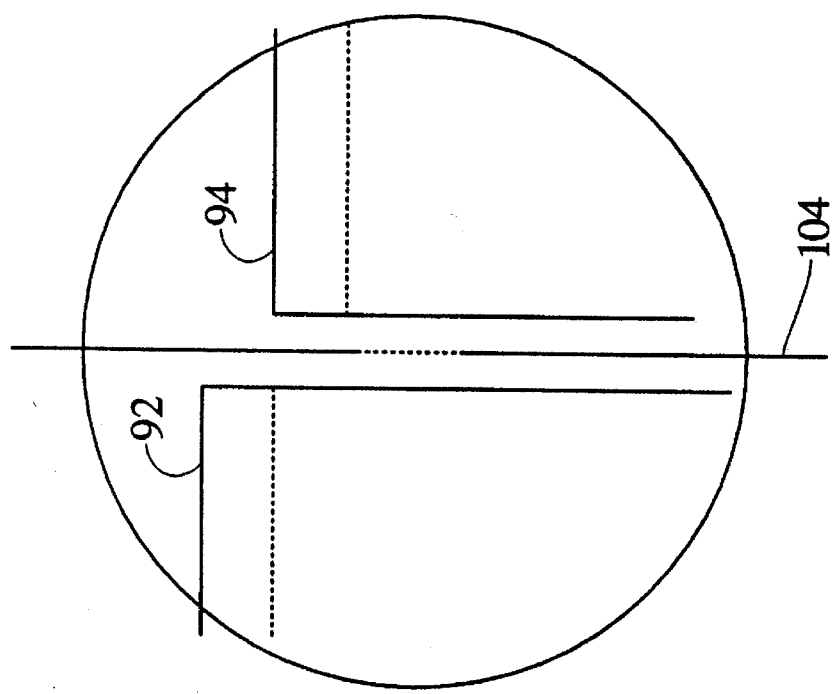
FIG. 5 is a partial cross sectional view of the ring tube collimator of an alternative embodiment of the x-ray tube of FIG. 2 in an open state wherein the fixed ring has a larger diameter than the adjustable ring.

In the alternate embodiment of FIGS. 5 and 6, movable ring 94 has a smaller diameter than the fixed ring 92. The two rings, 92 and 94 overlap to function as a shutter to absorb all x-radiation. The movable ring 94 is translated to a position beyond a center line 104, as shown.

The shutter function is primarily useful for service applications in which the x-ray tube is energized but radiation in the examination room is undesirable. The shutter effect described in connection with FIGS. 5 and 6 provides a significant advantage over known systems in which a separate shutter and collimator are used. The instant development reduces the necessity of incorporating two separate mechanisms into the x-ray thus increasing efficiency and reducing the number of mechanisms needed.

Figure 7:
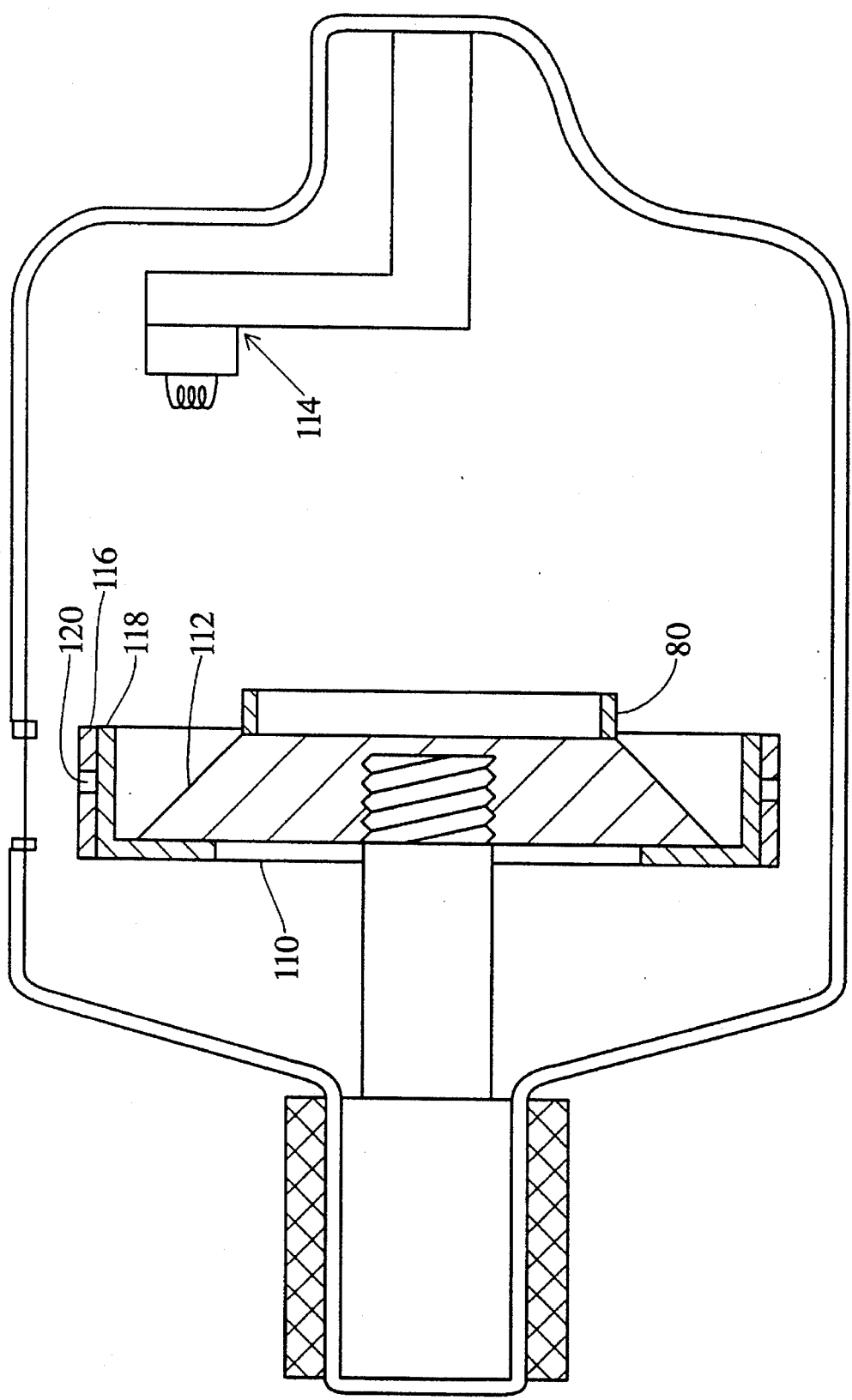

The present development has been described placing particular emphasis on an x-ray tube using a stationary ring anode and a rotating cathode. However, as shown in FIG. 7, features of the present application are also applicable to an x-ray tube utilizing a rotating anode 110 having an anode face 112 and a stationary cathode 114. An election beam is directed by cathode 114 to the anode face 112 to generate x-rays which are transmitted through a pre-collimator 116.

The pre-collimator 116, which is formed of a material having a high atomic number, is disposed on support structure, or ring, 118 so that a slot 120 can be formed in the pre-collimator 116 without the need for additional structure to support portions of the pre-collimator extending beyond the slot. The support structure 118 is preferably made of a material having a low atomic number.

The invention has been described with reference to preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An x-ray tube comprising:
   a generally toroidal housing having an evacuated annular interior;
   an annular anode mounted in the toroidal housing interior;
   a rotating frame rotatably disposed within the toroidal housing interior;
   at least one cathode assembly mounted to the frame for rotation therewith, the cathode assembly including an electron source forming an electron beam that strikes the anode to generate an x-ray beam;
   a pre-collimator supported within the evacuated annular interior of the toroidal housing, the precollimator having an x-ray passing slot; and,
   a collimator mounted outside of the evacuated annular interior of the toroidal housing for collimating the x-ray beam which passed through the precollimator slot.

2. The x-ray tube as set forth in claim 1 wherein the collimator includes a ring collimator supported by toroidal housing for collimating the x-rays into a beam, the collimator including a first ring and a second ring between which the x-ray beam is defined, the first and second rings having a common central axis, at least one of the first and second rings being adjustably mounted such that a distance between the first and second rings is adjustable.

3. An x-ray tube comprising:
   a generally toroidal housing having an evacuated annular interior;
   an annular anode mounted in the toroidal housing interior;
   a rotating frame rotatably disposed within the toroidal housing interior;
   at least one cathode assembly mounted to the frame for rotation therewith, the cathode assembly including an electron source forming an electron beam that strikes the anode to generate an x-ray beam;
   a precollimator supported in the toroidal housing interior having an x-ray passing slot, the pre-collimator being mounted on the rotating frame in alignment with at least one cathode assembly; and,
   a collimator for collimating the x-ray beam passing through the precollimator slot.

4. The x-ray tube as set forth in claim 3 further including a second pre-collimator supported by the anode, the second pre-collimator having a second slot for passage of the x-ray beam.

5. The x-ray tube as set forth in claim 4 further including a support ring of material having a low atomic number disposed between the second pre-collimator and the anode.

6. An x-ray tube comprising:
   a generally toroidal housing having an evacuated annular interior;
   an annular anode mounted in the toroidal housing interior;
   a rotating frame rotatably disposed within the toroidal housing interior;
   at least one cathode assembly mounted to the frame for rotation therewith, the cathode assembly including an electron source forming an electron beam that strikes the anode to generate an x-ray beam;
   a pre-collimator supported by the anode in the toroidal housing interior and having an x-ray passing slot; and,
   a collimator for collimating the x-ray beam passed through the precollimator slot.

7. The x-ray tube as set forth in claim 6 further including a support ring of a material having a low atomic number disposed between the pre-collimator and the anode.

8. An x-ray tube comprising:
   a generally toroidal housing having an evacuated annular interior;
   an annular anode mounted in the toroidal housing interior;
   a rotating frame rotatably disposed within the toroidal housing interior;
   at least one cathode assembly mounted to the frame for rotation therewith, the cathode assembly including an electron source forming an electron beam that strikes the anode to generate an x-ray beam;
   a precollimator supported in the toroidal housing interior having an x-ray passing slot;
   a shield ring attached around the anode on a side opposite the pre-collimator; and,
   a collimator for collimating the x-ray beam passed through the precollimator slot.

9. An x-ray tube comprising:
   a generally toroidal housing having an evacuated, annular interior;
   an annular anode mounted in the toroidal housing interior;

a rotating frame rotatably disposed within the toroidal housing interior;

at least one cathode assembly mounted to the rotating frame for rotation therewith, the cathode assembly including an electron source forming an electron beam that strikes the anode to generate x-rays;

a ring collimator supported by toroidal housing for collimating the x-rays into a beam, the collimator including a first ring and a second ring between which the x-ray beam is defined, the first and second rings having a common central axis, at least one of the first and second rings being adjustably mounted such that a distance between the first and second rings is adjustable, the first ring having a first diameter and the second ring having a second diameter, the first diameter being greater than the second diameter.

10. The x-ray tube as set forth in claim 9 further including a linear motion drive mechanism for selectively moving the first and second rings relative to each other to adjust the distance therebetween.

11. The x-ray tube as set forth in claim 9 further including a rotary motion drive for selectively moving the first and second rings relative to each other.

12. The x-ray tube as set forth in claim 11 wherein the second ring includes a line pitch screw threadingly disposed on a periphery thereof.

13. An x-ray tube comprising:

a generally toroidal housing having an evacuated, annular interior;

an annular anode mounted in the toroidal housing interior;

a rotating frame rotatably disposed within the toroidal housing interior;

at least one cathode assembly mounted to the rotating frame for rotation therewith, the cathode assembly including an electron source forming an electron beam that strikes the anode to generate x-rays;

a pre-collimator supported in the evacuated, annular interior of the toroidal housing, the precollimator having an x-ray passing slot disposed between the annular anode and the central axis such that x-rays pass through the precollimator prior to exiting the toroidal housing;

a ring collimator supported by toroidal housing for collimating the x-rays which passed through the precollimator slot into a beam, the collimator including a first ring and a second ring between which the x-ray beam is defined, the first and second rings having a common central axis, at least one of the first and second rings being adjustably mounted such that a distance between the first and second rings is adjustable.

14. The x-ray tube as set forth in claim 13 wherein the pre-collimator is mounted on the rotating frame for rotation therewith.

15. The x-ray tube as set forth in claim 13 wherein the pre-collimator is connected to the anode.

16. The x-ray tube as set forth in claim 13 further including an x-ray shield disposed on a side of the anode opposite the pre-collimator.

17. An x-ray tube comprising:

a generally toroidal housing having an evacuated, annular interior;

an annular anode mounted in the toroidal housing interior;

a rotating frame rotatably disposed within tho toroidal housing interior;

at least one cathode assembly mounted to the rotating frame for rotation therewith, the cathode assembly including an electron source forming an electron beam that strikes the anode to generate x-rays;

a ring collimator supported by toroidal housing for collimating the x-rays into a collimated x-ray beam centered on a central axis, the collimator including a first ring and a second ring between which the x-ray beam is defined, the first and second rings having a common central axis, at least one of the first and second rings being adjustably mounted such that a distance between the first and second rings is adjustable; and a means for controlling the first and second rings to adjust a width of the collimated x-ray beam by a selectively adjustable width and to translate the central axis of the collimated x-ray beam one-half of the selected width.

18. An CT scanner comprising:

a patient support for supporting a selected portion of a patient in an examination region;

an x-ray tube including:
  a generally toroidal housing having an evacuated interior;
  an annular anode mounted in the interior;
  a rotating frame rotatably disposed within the interior;
  at least one cathode assembly mounted to the frame for rotation therewith, the cathode assembly including an electron source forming an electron beam that strikes the anode to generate an x-ray beam;
  a precollimator mounted in a fixed relationship to the anode in the evacuated interior for limiting a cross-section dimension of the x-ray beam subsequent to generation thereof; and,
  a collimator for collimating the x-ray beam of limited cross-sectional dimension from the precollimator.

19. A CT scanner comprising:

a patient support for supporting a selected portion of a patient in an examination region;

an x-ray tube including:
  a generally toroidal housing having an evacuated interior and extending around a central axis;
  an annular anode mounted in the interior;
  a rotating frame rotatably disposed within the evacuated interior;
  at least one cathode assembly mounted to the rotating frame for rotation therewith, the cathode assembly including an electron source forming an electron beam that strikes the anode along a circular path to generate x-rays, the circular path defining a first plane orthogonal to the central axis;
  an annular x-ray window mounted in the housing facing toward the central axis through which the x-rays are passed;

a ring of x-ray detectors extending around the toroidal housing adjacent and axially offset from the annular x-ray window, the x-ray detectors defining a second plane that is parallel to and displaced from the first plane;

a precollimator supported within the toroidal housing evacuated interior between the annular anode and the annular window;

a ring collimator including a first ring and a second ring, the first and second rings being disposed on opposing sides of the annular window, the ring collimator and the precollimator interacting to define an x-ray beam that originates at the anode in the first plane, crosses the central axis, and intersects the detectors at the second plane.

20. An x-ray tube comprising:

an evacuated housing;

an anode assembly disposed in the evacuated housing, the anode assembly having an annular anode track therearound;

a cathode assembly mounted in the evacuated housing for forming a beam of electrons that strike the anode track to generate x-rays; and, a ring of x-ray blocking material mounted to the anode and extending around the anode track.

21. The x-ray tube as set forth in claim 20 wherein the ring of x-ray blocking material has a narrow, annular x-ray passing window therein such that a beam of x-rays pass therethrough.